United States Patent [19]
Newcomb et al.

[11] Patent Number: 6,119,276
[45] Date of Patent: Sep. 19, 2000

[54] SPORT GOGGLE

[75] Inventors: Robert L. Newcomb, Ketchum, Id.; Thomas E. Meyerhoffer, Montera, Calif.

[73] Assignee: Smith Sport Optics, Inc., Ketchum, Id.

[21] Appl. No.: 09/089,846

[22] Filed: Jun. 3, 1998

[51] Int. Cl.⁷ ........................................................ A42B 3/24
[52] U.S. Cl. ........................................................ 2/425; 2/436
[58] Field of Search .............................. 2/425, 424, 436, 2/437, 439, 431, 432, 440, 447, 171.3

[56] References Cited

U.S. PATENT DOCUMENTS

| | | | |
|---|---|---|---|
| 4,435,852 | 3/1984 | Nesler | 2/436 |
| 4,698,856 | 10/1987 | Arai | 2/171.3 X |
| 4,977,627 | 12/1990 | Metcalfe et al. | 2/437 |
| 5,815,848 | 10/1998 | Jarvis | 2/425 X |
| 5,867,841 | 2/1999 | Chiang | 2/439 X |

*Primary Examiner*—Peter Nerbun
*Attorney, Agent, or Firm*—Dorsey & Whitney LLP

[57] ABSTRACT

A sport goggle and a system for ventilating a sport goggle is shown and described. The sport goggle has a strap, a lens structure, and a frame having a first edge extending laterally across the wearer's forehead. The first edge is shaped such that a portion of the first edge is curved in a concave up direction when the sport goggle is in a position of use, and such that, when the sport goggle is worn in combination with a helmet, one or more gaps are created between the first edge and a second edge on the front of the helmet. The first edge has a first opening located to allow air to flow into the goggle chamber. Increased goggle ventilation through the first opening can be caused by either the concave up portion of the first edge, or the gaps between the first and second edges.

15 Claims, 3 Drawing Sheets

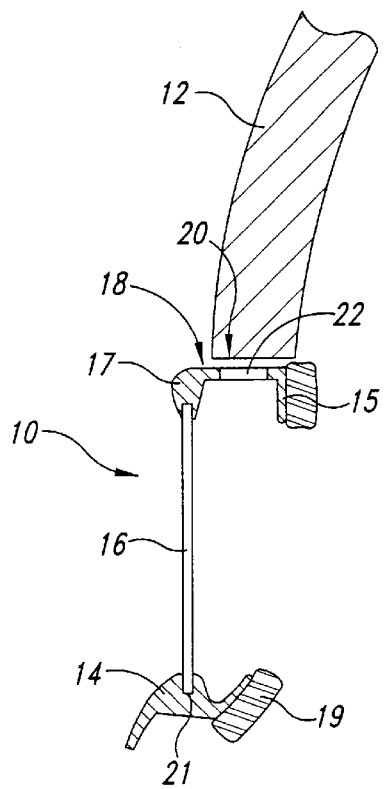
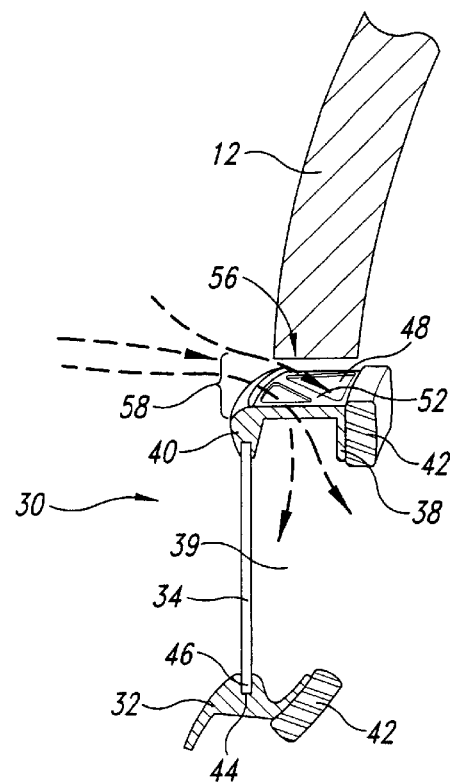
Fig. 4
(PRIOR ART)
Fig. 5
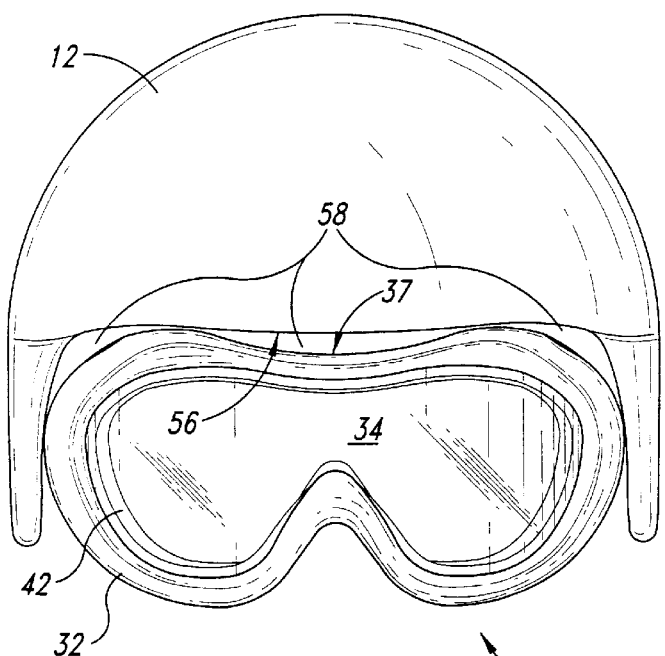
Fig. 6

SPORT GOGGLE

TECHNICAL FIELD

The invention is directed toward a sport goggle and, more particularly, to a sport goggle with increased ventilation to reduce fogging of the lens structure during use, particularly when worn with a protective helmet.

BACKGROUND OF THE INVENTION

Individuals often wear goggles to protect their eyes or to improve their vision when participating in a sport or a recreational activity, such as skiing or motorcycle racing. FIGS. 1 and 4 show a typical goggle 10 of the prior art when worn in conjunction with a protective helmet 12. The goggle 10 has a frame 14, a lens structure 16, and a strap (not shown). The frame 14 encircles both of the wearer's eyes, rests on or above the wearer's nose, and has a generally horizontal section running across the wearer's forehead. The frame 14 has an inner section 15 that rests against the wearer's face, and an outer section 17 adapted to hold the lens structure 16. The inner section 15 of the frame 14 can be conformed to rest closely against the wearer's face, and can be lined with a cushion 19 to make it more comfortable. The outer section 17 of the frame 14 is formed with a groove 21 to receive the perimeter of the lens structure 16.

The lens structure 16 of the goggle 10 typically has a thin perimeter edge that is retained within the groove 21 in the outer section 17 of the frame 14. The lens structure 17, which may be single- or double-pane, is separated from the wearer's face by the thickness of the frame 14. A chamber of air is formed in the space within the frame 14 that lies between the lens structure 16 and the wearer's face.

The strap holds the goggle 10 in place on the wearer's head. The strap is typically made from an elastic material, and can be adjustable to fit a variety of individuals.

When an individual first puts on the goggle 10, the air within the chamber is the same temperature, and has the same relative humidity, as the air surrounding the goggle 10. Under these conditions, the lens structure 16 is transparent and the wearer can perform the sport or activity with full vision.

As time passes, moisture evaporating from the wearer's face increases the relative humidity of the air in the chamber. As the relative humidity increases, so does the dew point, or the point at which water molecules will condense from a vapor phase to a liquid phase. When cold air surrounding the goggle 10 reduces the temperature of the lens structure 16 to a temperature below the dew point, water will condense on the inner surface of the lens structure 16. The condensate on the inner surface of the lens structure 16 decreases the wearer's vision and makes it more difficult, or impossible, for the wearer to participate in the sport or activity.

Over the last few decades, numerous modifications and innovations have been developed with mixed success in an attempt to solve the problem of fogging goggles. These include: providing passive air vents in the frame to allow fresh air to circulate into the chamber; providing fans or the like to force fresh air into the chamber (not shown); providing double-paned lenses to insulate the internal surface of the lens structure from the cold, external temperature (not shown); and wiping the lens structure with "no fog" cloths carrying chemicals designed to prevent dew formation (not shown).

The "no fog" cloth only lasts for a short period of time before the chemical is dispersed or evaporates and the cloth must be replaced. If the cloth is used after the chemical has run out, it is no better than a shirt sleeve for the temporary fix of wiping off the fog. Even worse, the cloth is often lost or misplaced before the chemical runs out. The cloth is therefore a burden, and can become expensive if numerous replacements are purchased.

The forced air fans are an expensive addition to a goggle, significantly increasing its retail price. In addition, the fan, motor and batteries are heavy and can make the goggle uncomfortable. Also, when the batteries run out, the fan unit is worthless.

Double-paned lenses may delay the problem of fogging, but if the outside temperature is low enough, the internal lens will eventually drop to a temperature below the dew point. The colder weather, the faster the change. Consequently, if the weather is extremely cold, the double-paned lenses have substantially the same problem as single-paned lenses.

The simple, passively vented goggles 10 have proven to be a decent solution, but are problematic as well. This type of goggle 10 typically operates by having a number of vents 22 around the perimeter of the goggle 10. If the wearer is participating in an activity that entails high speeds, such as skiing, snowboarding, cycling, motorcycling, snowmobiling, etc., the air moving past the wearer's face can enter the goggle 10 through one or more of the vents 22, replacing the moist air in the chamber with less humid, outside air.

The primary problem with these types of goggles 10 is that the shape of the frame 14 is not conducive to air flow through the vents 22. Ventilated goggles 10 usually have vents 22 along their top edge 18 and bottom edge (not shown). In order to keep these edges from blocking or overly reducing the field of view of the wearer, however, these edges are generally oriented parallel to the direction of sight, which usually corresponds to the direction of travel. Consequently, if a wearer is looking straight forward, all of the vents 22 along the edges of the goggle are facing in a direction roughly normal to the direction of the air flow. This orientation is the least likely to allow for circulation of air.

In addition, the top edge 18 of most goggles 10 is slightly curved in a convex-up direction with respect to the orientation of use of the goggle 10. This has become the shape of substantially every goggle 10 on the market due presumably to the demands of appearance and ease of manufacturing. Ironically, this common curvature may lessen the air flow through the vents 22. If the wearer is looking slightly downward, which is the most common head orientation in all of the above-listed activities, the convex curvature of the top edge 18 on the goggle 10 may direct the air flow around the sides of the goggle 10. This further decreases ventilation in the goggle 10.

These problems are exacerbated when the individual is also wearing a protective helmet 12. The top edge 18 runs in a substantially horizontal direction across the forehead of the individual wearing the goggle 10. The top edge 18 is thus roughly parallel to an adjacent front edge 20 on the protective helmet 12. The gap between the top edge 18 and the front edge 20 is too narrow for a sufficient amount of air to flow through and ventilate the goggle 10. Consequently, air rushing past the wearer's face is forced either over the top of the individual's head or around the sides of the protective helmet 12.

A need therefore exists for an improved sport goggle with increased ventilation to reduce lens fogging during use, particularly when the goggle is worn in conjunction with a protective helmet.

SUMMARY OF THE INVENTION

The invention is directed to a sport goggle having increased ventilation characteristics, and to a system for creating increased ventilation in the sport goggle, particularly when worn with a protective helmet. The sport goggle incorporates a frame, a lens structure, and a strap. The frame has an outer section adapted to receive the lens structure and an inner section adapted to contact the wearer's face. The outer section can have a continuous groove in which a perimeter edge of the lens structure can be retained. The inner section can be molded or otherwise shaped to conform closely to the wearer's face. The inner section can also be coated with a soft, cushioning material, such as foam, to make it more comfortable for the wearer. The area within the frame of the sport goggle is defined as a goggle chamber.

The frame also has a first edge extending generally laterally across the wearer's forehead when the sport goggle is worn. The first edge can be formed as a complex curve in which at least a portion of the first edge is in a concave-up direction as defined when the sport goggle is being worn. In the preferred embodiment, the concave-up portion is at the center of the first edge.

The outer section of the frame can be separated from the inner section of the frame to define an opening at one or more points on the perimeter of the frame. A first opening can be positioned along the first edge of the frame and, in a preferred embodiment, is positioned about the center of the first edge. Additional openings can be spaced about the perimeter of the frame to allow additional air to flow into or out of the goggle chamber. At points intermediate the openings, one or more ribs can extend from the outer section of the frame to the inner section of the frame to provide additional strength. A strip of foam or similar material can be positioned over the opening to prevent dirt or particulates from entering the goggle chamber.

The lens structure is one or more transparent sheets of material, preferably plastic. The perimeter edge of the lens structure is adapted to engage the outer section of the frame. In the preferred embodiment, the perimeter edge is adapted to slidably engage the groove in the outer section. The lens can be clear or it can be tinted to filter out light between particular wavelengths.

The strap holds the sport goggle in the proper position for use on an individual's face. The strap is typically made from a length of elastic material to urge the inner surface of the frame against the wearer's face. The strap can also be woven through a buckle to allow the sport goggle to be adjustable for use by individuals with various sized heads.

The sport goggle may be worn by an individual with or without a protective helmet. The strap holds the sport goggle against the individual's face with the first edge running substantially horizontally across the wearer's forehead. The first opening in the frame is positioned centrally to, and corresponds with the location of the concave-up portion of the first edge. Additional openings can be positioned on either side of the wearer's nose, on a portion of the frame separate from the first opening.

When the wearer is in a position to perform one of the above-listed sports, the head may be facing forward and is rotated slightly downward so that the eyes can see the approaching terrain. When the sport goggle is worn without a helmet, the air rushes at the individual's face and against the first edge of the sport goggle. The concave-up portion of the goggle can create an area of higher pressure directly above the first edge of the goggle. The increase in air pressure can force air into the first opening. The air entering the chamber can force the air that was already in the chamber out of the additional openings in the frame. This air transfer ventilates the goggle chamber, and can replace air having a comparably higher relative humidity with air having a comparably lower relative humidity.

When worn with a protective helmet, the sport goggle itself can be substantially identical in structure and position with respect to the wearer as described above. The wearer can put on the sport goggle either before or after the protective helmet, the primary difference being that the strap is positioned either inside or outside the protective helmet, respectively. The protective helmet is positioned at the top of the wearer's head, and a second edge on the protective helmet runs generally laterally across the wearer's forehead.

When the wearer is performing one the sports or activities described above, the individual is in the same position as described in the prior embodiment. In this case, however, the second edge of the protective helmet is positioned adjacent the first edge of the sport goggle. In this embodiment, the complex curvature of the first edge, when juxtaposed with the second edge of the protective helmet, creates one or more gaps between the two edges. These gaps can allow substantial amounts of air to enter the first opening. As described above, this air flow can ventilate the goggle.

The concave-up portion of the frame preferably is central to the first edge, thereby creating a large gap at the center of the frame. This location can correspond to the position of the first opening, and can optimize the ventilation of the goggle chamber.

The sport goggle may also be attached to the protective helmet in the same relative position as it is in the prior embodiment. The sport goggle and protective helmet in this embodiment can be put on and taken off as a unit. In all other aspects, the sport goggle and protective helmet in this embodiment function substantially identically to the prior embodiment.

BRIEF DESCRIPTION OF THE DRAWINGS

FIG. 4 is a partial sectional view of a goggle and protective helmet according to the prior art.

FIG. 5 is a partial sectional view of a sport goggle and protective helmet according to an embodiment of the present invention.

FIG. 6 is a front elevation view of a sport goggle and protective helmet according to an embodiment of the present invention.

DETAILED DESCRIPTION OF THE INVENTION

The present invention is directed toward a sport goggle having increased ventilation characteristics, and to a system for creating increased ventilation in the sport goggle, particularly when worn with a protective helmet. Many specific details of certain embodiments of the invention are set forth in the following description and in FIGS. 2, 3, 5 and 6 in order to provide a thorough understanding of such embodiments. One skilled in the art, however, will understand that the present invention may have additional embodiments, or that the invention may be practiced without several of the details described in the following description.

Figure 2:
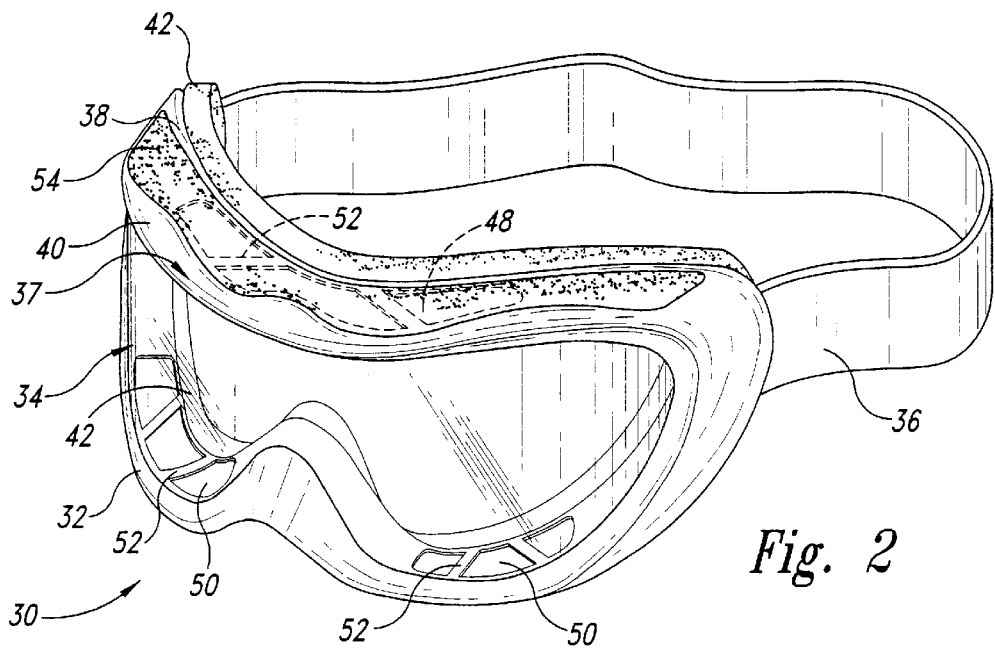
FIG. 2 is an isometric view of a sport goggle according to an embodiment of the present invention.

FIG. 2 shows a sport goggle 30 according to one embodiment of the present invention. The sport goggle 30 incorporates a frame 32, a lens structure 34 which is retained within the frame 32, and a strap 36 which holds the sport goggle 30 on a wearer's head. The frame 32 has a first edge 37 that crosses the wearer's forehead in a generally lateral direction. The frame 32 encircles both of the wearer's eyes and is curved to rest on or above the wearer's nose. When the sport goggle 30 is worn, an enclosed goggle chamber 39 is created within the frame 32 and between the lens structure 34 and the wearer's face (FIG. 5).

The first edge 37 has the shape of a complex curve. In the preferred embodiment, the first edge 37 is curved to conform with the wearer's forehead, and is also curved such that the center of the first edge 37 has a concave-up curvature as defined when the sport goggle 30 is being worn (FIG. 6). The first edge 37 can have a wide variety of shapes, but is preferably symmetrical with respect to the axis of bilateral symmetry of the wearer's head. The side portions of the first edge 37 are preferably curved in a concave down direction.

The frame 32 has an inner section 38 that is contoured to contact the wearer's face, and has an outer section 40 that is adapted to receive the lens structure 34. The inner section 38 can be a resilient material, such as rubber or plastic, and it can be flared to allow the sport goggle 30 to better conform to the wearer's face. The inner section 38 can also be lined with a soft cushion 42, such as foam, to make the sport goggle 30 more comfortable for the wearer.

The outer section 40 has a curvature roughly parallel to the inner section 38. The outer section 40 can have a groove 44 about some or all of its innermost surface that is adapted to receive a perimeter edge 46 of the lens structure 34 (FIG. 5). The material of the frame 32 can be sufficiently resilient to allow the wearer to distort the frame 32 to receive the perimeter edge 46 of the lens structure 34 within the groove 44. The resilient nature of the frame 32 also allows the wearer to replace the lens structure 34 when broken, or to switch to a different lens structure 34 based on light, sun, and visibility conditions.

The outer section 40 of the frame 32 can be separated from the inner section 38 to create a first opening 48 to allow air to flow into the goggle chamber 39. In the preferred embodiment, the first opening 48 is positioned about the center of the first edge 37. The first opening 48 can extend across all or a portion of the first edge 37. One or more ribs 52 can extend from the inner section 38 to the outer section 40 across the first opening 48 to provide additional strength to the frame 32. The first opening 48 can be covered by an open-celled, foam strip 54 or a similar material that will allow air to pass through, but can prevent particulates from passing through.

The frame 32 can have one or more additional openings 50 at locations along the perimeter of the frame 32 distant from the first opening 48. The air flowing into the goggle chamber 39 through the first opening 48 can force air that was previously in the goggle chamber 39 out of the additional openings 50. This flow of air can ventilate the sport goggle 30, and can decrease, or possibly prevent, fogging of the lens structure 34.

The lens structure 34 is a transparent material constructed to complement the shape of the outer section 40 of the frame 32. As described above, the perimeter edge 46 of the lens structure 34 engages the groove 44 in the outer section 40 of the frame 32. In the preferred embodiment, the lens structure 34 is plastic. The lens structure 34 can be clear or it can be tinted to filter out certain wave lengths of light.

The strap 36 retains the sport goggle 30 in the proper position for use against a wearer's head. The ends of the strap 36 are engaged with opposing sides of the sport goggle 30. The strap 36 can be an elastic material biased to urge the sport goggle 30 against the wearer's face, and can be woven through a buckle or similar article to allow the length of the strap 36 to be adjusted.

Figure 1:
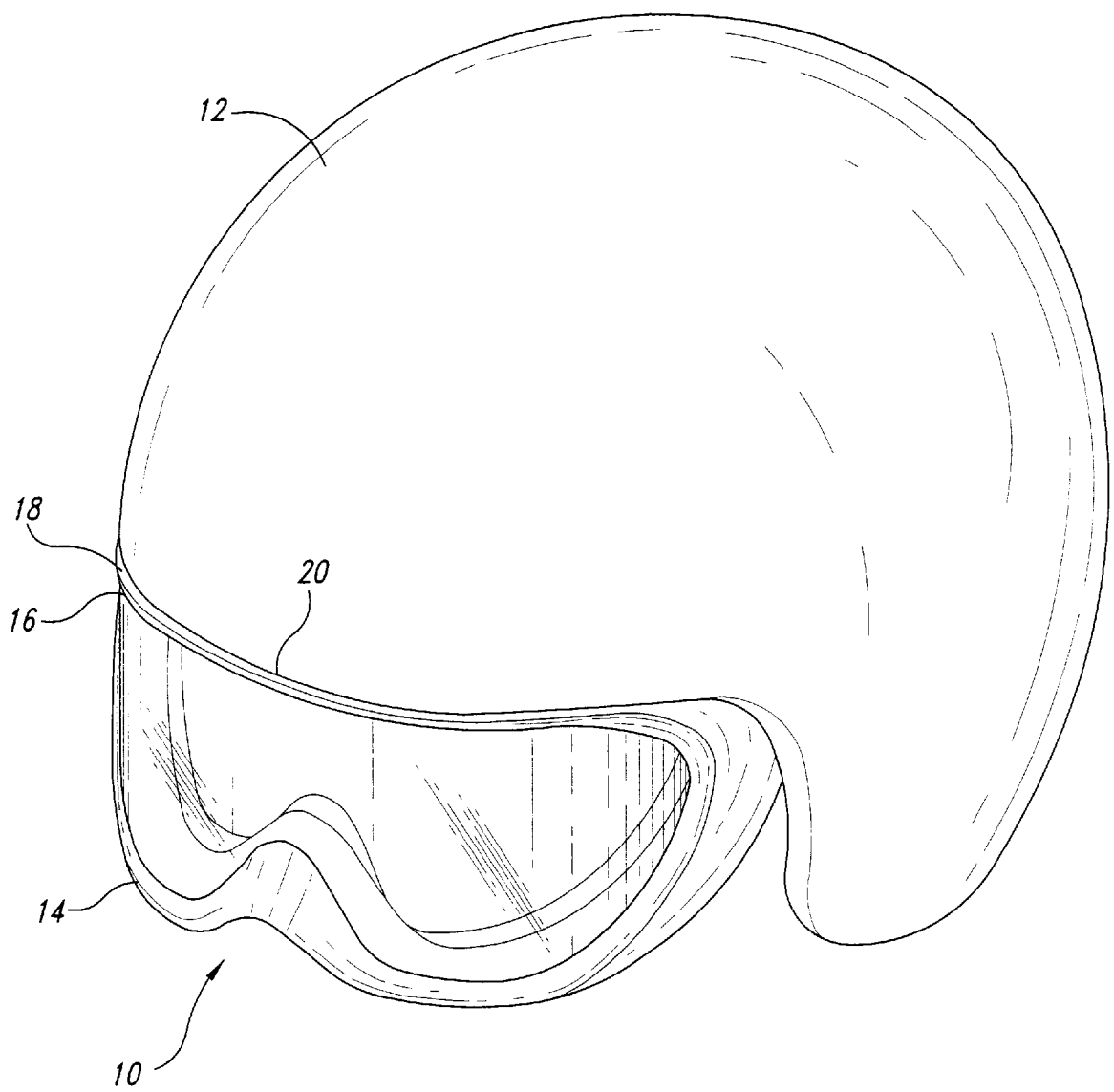
FIG. 1 is an isometric view of a goggle and protective helmet according to the prior art.
Figure 3:
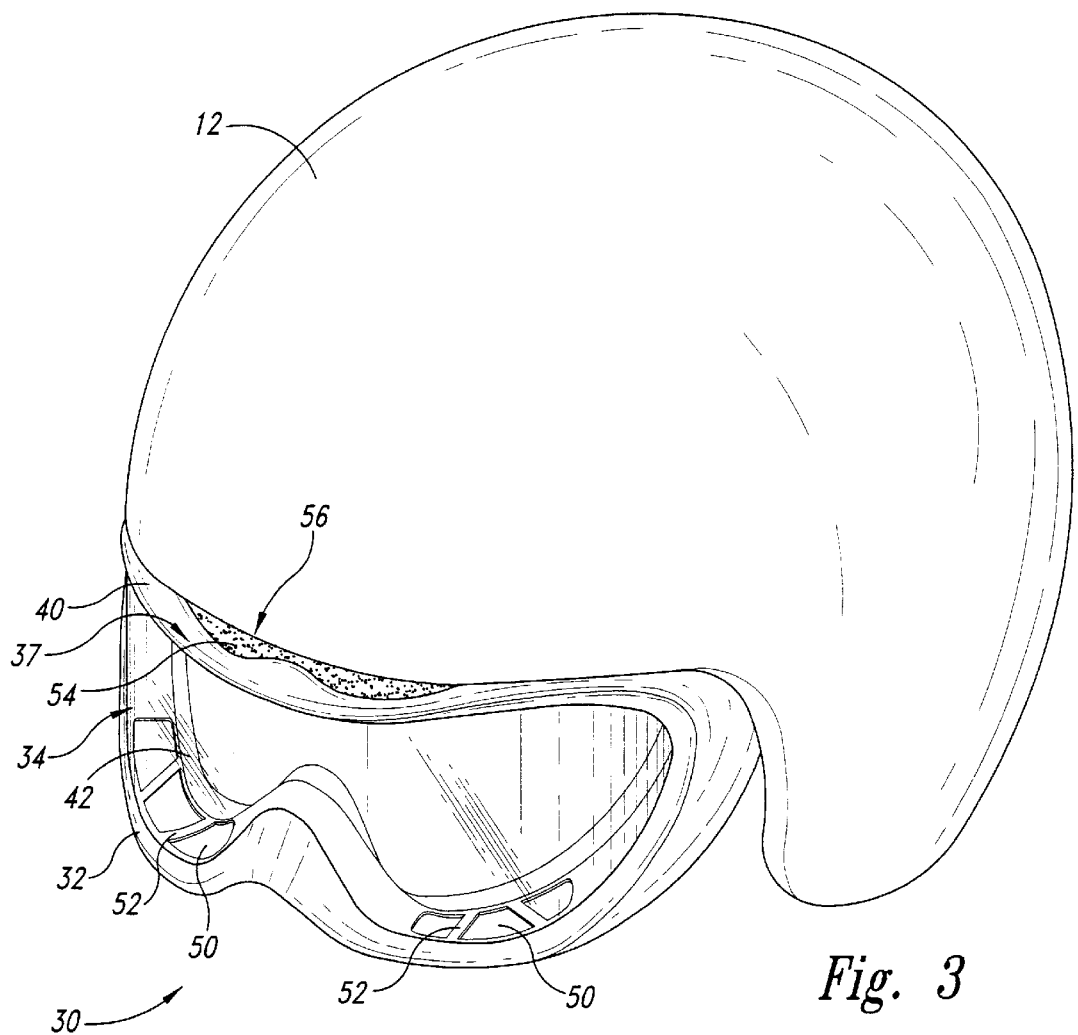
FIG. 3 is an isometric view of a sport goggle and protective helmet according to an embodiment of the present invention.

During operation, the sport goggle 30 is worn in the same manner as a conventional goggle 10 of the prior art (FIG. 1). As illustrated in FIGS. 3, 5, and 6, the sport goggle 30 may be worn in combination with a protective helmet 12. The protective helmet 12 is worn in the typical fashion, with a second edge 56 extending laterally across the wearer's forehead. The wearer can put on the sport goggle 30 either before or after putting on the protective helmet 12. When the protective helmet 12 and sport goggle 30 are worn in combination, the first edge 37 of the sport goggle 30 abuts the second edge 56 of the protective helmet 12.

The complex shape of the first edge 37 spaces the sport goggle 30 apart from the protective helmet 12. More specifically, the complex shape of the first edge 37, when abutted against the generally horizontal shape of the second edge 56, creates one or more gaps 58 through which air can flow into the first opening 48 and into the goggle chamber 39. FIG. 5 best illustrates the flow of air through one of the gaps 58 and into the goggle chamber 39. In the preferred embodiment, a gap 58 is positioned at the center of the first edge 37, directly above the first opening 48. Additional gaps 58 can be located at various locations along the first edge 37.

In contrast to the prior art, the gaps 58 between the sport goggle 30 and the protective helmet 12 are large enough to allow sufficient air to ventilate the goggle chamber 39 and decrease the likelihood and/or duration of fogging. In the prior art, the complementary shapes of the top edge 18 and the front edge 20 prevented sufficient air from flowing into the goggle chamber, allowing fog to further interfere with the wearer's vision.

The sport goggle 30 may also be worn without a protective helmet 12. When the wearer moves in a forward direction while looking slightly downward at the approaching terrain, the air flowing past the wearer's head impinges both the wearer's forehead and the first edge 37 of the sport goggle 30. The concave-up portion at the center of the first edge 37 may deflect the air toward the center of the first edge 37. The deflection of air can create an area of slightly higher pressure, the air pressure forcing air into the first opening 48. The air entering the first opening 37 forces air that was inside the goggle chamber 39 to exit one of the additional openings 50. The foam strip 54 covering the first opening 37 is porous enough to allow air to flow through it and into the goggle chamber 39, but can prevent most dirt or other particulates from entering the goggle chamber 39.

From the foregoing it will be appreciated that, although specific embodiments of the invention have been described herein for purposes of illustration, various modifications may be made without deviating from the spirit and scope of the invention. Accordingly, the invention is not limited except as by the appended claims.

We claim:

1. A system for creating increased ventilation in a sport goggle comprising:

a lens structure;

a sport goggle frame having a first edge positioned to extend laterally across a forehead when the sport goggle is worn, the frame having an outer section adapted to receive the lens structure and an inner section adapted to mate with a face, the outer section being separated from the inner section along a portion of the first edge to define a first opening; and a helmet having a second edge positioned to be adjacent the first edge when the helmet is worn, at least a portion of the first edge being nonparallel to the second edge to create a gap between the first and second edges such that fresh air can flow into the gap and the first opening.

2. The system of claim 1 further comprising a second opening at a point on the perimeter of the frame distant from the first opening such that fresh air entering the sport goggle through the first opening can flush moist air out of the second opening.

3. The system of claim 1 wherein the first edge is nonparallel to the second edge at locations that are equally spaced from the center of the first edge.

4. The system of claim 1 wherein the second edge comprises at least a crossing portion oriented to lie in a transverse direction across a wearer's forehead during use, and wherein the first edge of the frame is positioned to extend laterally across the wearer's forehead when the sport goggle is worn, the first edge having at least a first contact portion and at least a first vent portion, the frame having an outer section adapted to receive the lens structure and an inner section adapted to contact the wearer's face, the outer section being spaced apart from the inner section along the vent portion of the first edge to define a first opening therebetween, the first edge being shaped such that the first contact portion of the first edge is positionable against the crossing portion of the second edge of the helmet and the vent portion of the first edge is adapted to be permanently spaced apart from the crossing portion of the second edge of the helmet to create a gap through which fresh air can flow between the first and second edges and into the sport goggle through the first opening.

5. The system of claim 4 wherein the shape of the first edge is a complex curve.

6. The system of claim 4 further comprising a second opening at a point on the frame spaced apart from the first opening such that fresh air entering the sport goggle through the first opening can flush moist air out of the second opening.

7. The system of claim 4 wherein the vent portion of the first edge is at the center of the first edge.

8. The system of claim 4 wherein a central portion of the first edge is configured to be spaced apart from the second edge and is curved in a concave up direction as defined when the sport goggle is in a position of use.

9. The system of claim 8 wherein the first edge is bilaterally symmetrical with respect to a vertical axis.

10. The system of claim 9 wherein at least one side portion of the first edge is curved in a concave down direction as defined when the sport goggle is in a position of use.

11. The system of claim 1 wherein the second edge comprises at least a crossing portion oriented to laterally cross a wearer's forehead during use, and wherein the first edge of the frame is positioned to extend laterally across the wearer's forehead when the sport goggle is worn, the frame having an outer section adapted to receive the lens structure and an inner section adapted to contact the wearer's forehead, the outer section being separated from the inner section along at least a venting portion of the first edge to define a first opening therebetween, the first edge forming a space defined by the curvature of the first edge when abutted against the second edge of the helmet, and the first edge being configured to contact the crossing portion of the second edge of the helmet during use and to maintain separation between the first and second edges along at least the venting portion of the first edge to create a gap through which fresh air can flow between the first and second edges and into the sport goggle through the first opening.

12. The system of claim 11 wherein the space is in the shape of a complex curve extending across a portion of the second edge.

13. The system of claim 12 wherein the complex curve comprises a plurality of vertices, the vertices being arranged such that one or more of the vertex is oriented to abut the second edge.

14. The system of claim 13 wherein a central portion of the first edge is configured to be spaced from the second edge and is curved in a concave up direction as defined when the sport goggle is in a position of use.

15. The system of claim 14 wherein the first edge is bilaterally symmetrical with respect to a vertical axis.

* * * * *